United States Patent [19]

Nevitt et al.

[11] 4,451,685

[45] May 29, 1984

[54] PROCESS TO CONVERT $C_2$-$C_3$ OLEFINS TO A GASOLINE BLENDING STOCK

[75] Inventors: Thomas D. Nevitt, Naperville; Norman F. Jerome, Elmhurst, both of Ill.

[73] Assignee: Standard Oil Company (Indiana), Chicago, Ill.

[21] Appl. No.: 485,228

[22] Filed: Apr. 15, 1983

Related U.S. Application Data

[63] Continuation of Ser. No. 422,744, Sep. 24, 1982, abandoned.

[51] Int. Cl.³ .......................... C07C 3/00; C07C 3/03; C07C 3/62
[52] U.S. Cl. ......................... 585/415; 502/64; 502/202; 585/417; 585/510; 585/520; 585/525; 585/664; 585/670

[58] Field of Search ............... 585/312, 322, 329, 415, 585/417, 418, 419, 510, 520, 525, 531, 664, 666, 670, 671; 252/432

[56] References Cited

U.S. PATENT DOCUMENTS

| | | | |
|---|---|---|---|
| 4,268,420 | 5/1981 | Klotz | 585/408 |
| 4,269,813 | 5/1981 | Klotz | 502/202 |
| 4,285,919 | 8/1981 | Klotz et al. | 502/202 |
| 4,292,438 | 9/1981 | Klotz | 562/503 |

*Primary Examiner*—Delbert E. Gantz
*Assistant Examiner*—A. Pal
*Attorney, Agent, or Firm*—Wallace L. Oliver; William T. McClain; William H. Magidson

[57] ABSTRACT

A process to convert propylene to gasoline blending stock products comprises contacting $C_2$-$C_3$ olefins under conversion conditions with an AMS-1B crystalline borosilicate catalyst composition.

15 Claims, No Drawings

PROCESS TO CONVERT $C_2$-$C_3$ OLEFINS TO A GASOLINE BLENDING STOCK

This application is a continuation application of U.S. Pat. application Ser. No. 422,744, filed Sept. 24, 1982, now abandoned.

BACKGROUND OF THE INVENTION

This invention relates to conversion of $C_2$-$C_3$ olefins and more particularly relates to conversion of propylene to higher value hydrocarbons such as a gasoline blending stock using an AMS-1B crystalline borosilicate-based catalyst.

Ethylene and propylene are widely available feedstocks.

Propylene is a common by-product in refinery processes, and, as such, is a relatively inexpensive refinery feedstock. It would be desirable to convert such a feedstock to a gasoline blending stock containing $C_4$-$C_8$ aliphatic products and $C_6$-$C_9$ aromatics.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolite Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420 and 4,269,813 incorporated by reference herein. According to these patents AMS-1B can be synthesized by crystallizing a source of an oxide of silicon, an oxide of boron, an oxide of sodium and an organic template compound such as a tetra-n-propylammonium salt. The process of this invention uses AMS-1B crystalline borosilicate molecular sieve.

Hydrocarbon conversion processes are known using other zeolitic materials. Examples of such processes are dewaxing of oil stock (U.S. Pat. Nos. 3,852,189, 4,211,635 and 28,398); conversion of lower olefins (U.S. Pat. Nos. 3,965,205 and 3,960,978 and European patent application No. 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocarbons (U.S. Pat. Nos. 3,753,891, 3,767,568, 3,770,614 and 4,032,432); conversion of ethane to aromatics and $C_3+$ hydrocarbons (U.S. Pat. No. 4,100,218); conversion of straight-chain and slightly branched-chain hydrocarbons to olefins (U.S. Pat. Nos. 4,309,275 and 4,309,276); and conversion of $C_4$ paraffins to aromatics (U.S. Pat. No. 4,291,182).

In a typical embodiment using the process of this invention, a propylene-propane stream from a refinery vapor recovery unit combined with hydrogen can be passed over an AMS-1B crystalline borosilicate-based catalyst. Because the reaction is highly exothermic, little heat input to a reactor is required. Products from such reactor can be sent to a distillation unit where propane and lighter hydrocarbon can be separated and $C_4+$ hydrocarbons can be added to gasoline.

Products resulting from the process of this invention generally are $C_4$-$C_8$ aliphatics and $C_6$-$C_9$ aromatics. Production of $C_1$-$C_2$ products typically is minimized especially at lower process temperatures such as around 350° to about 400° C. The process of this invention especially is desirable if $C_5$-$C_8$ aliphatic products are desired.

SUMMARY OF THE INVENTION

A process to convert propylene to gasoline blending stock products comprises contacting $C_2$-$C_3$ olefins under conversion conditions with an AMS-1B crystalline borosilicate catalyst composition.

BRIEF DESCRIPTION OF THE INVENTION

This invention is a method to convert $C_2$-$C_3$ olefins to a mixture of alkanes, alkenes, branched alkanes and alkenes, and aromatics useful as gasoline blending stock. More particularly, this invention is a method to convert $C_2$-$C_3$ olefins to a mixture containing $C_4$-$C_8$ aliphatics and $C_6$-$C_9$ aromatics using an AMS-1B crystalline borosilicate-based catalyst system.

Olefins used in the process of this invention can be in the presence of other substances such as other hydrocarbon-based molecules. Thus, a feedstream used in the process of this invention comprising propylene also can contain other hydrocarbons such as methane, ethane, propane, hydrogen, and inert gases. A process in which partially reacted hydrocarbons are recycled will contain a mixture including alkanes, alkenes, methane and aromatics. Typically an olefin feedstream used in this invention contains about 1 to 100 wt.% olefin and preferably contains about 50 to 100 wt.% olefin. The preferable olefin is propylene.

The catalyst useful in this invention is based on the crystalline borosilicate molecular sieve, AMS-1B, described in U.S. Pat. Nos. 4,268,420 and 4,269,813, incorporated herein by reference. A particularly useful catalyst for this invention contains AMS-1B in which a noble metal is placed by impregnation, ion exchange or other means.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$0.9 \pm 0.2 \, M_{2/n}O:B_2O_3:ySiO_2:zH_2O$ wherein M is at least one cation, n is the valence of the cation, y is between 4 and about 600 and z is between 0 and about 160.

TABLE I

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak;
W = weak;
M = medium;
MS = medium strong;
VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
|---|---|---|---|
| $SiO_2/B_2O_3$ | 5–400 | 10–150 | 10–80 |
| $R_2O^+/[R_2O^+ + M_{2/n}O]$ | 0.1–1.0 | 0.2–0.97 | 0.3–0.97 |
| $OH^-/SiO_2$ | 0.01–11 | 0.1–2 | 0.1–1 |
| $H_2O/OH^-$ | 10–4000 | 10–500 | 10–500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blendor. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propyl-ammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of silicic acid polymer (Ludox) are added with intensive mixing, preferably the pH is again checked and adjusted to a range of about 11.0±0.2. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°–200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Specific additional catalytic materials include ions and compounds of copper, lanthanum, molybdenum, cobalt, tungsten, nickel and zinc. Other additional catalytic materials can be ions and compounds of scandium, yttrium, titanium, zirconium, hafnium, vanadium, niobium, tantalum, chromium, cerium, manganese, iron and cadmium.

Groups of elements referred to herein are those contained in the Periodic Table of Elements, Handbook of Chemistry and Physics, 54th Edition, CRC Press (1973).

Ion exchange and impregnation techniques are well-known in the art. Typically, an aqueous solution of a cationic species is exchanged one or more times at about 25° to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition may be detrimental to catalytic activity.

The amount of catalytically active material placed on the AMS-1B borosilicate can vary from about 0.01 weight percent to about thirty weight percent, typically from about 0.1 to about 25 weight percent, depending on the process use intended. The optimum amount can be determined easily by routine experimentation.

The AMS-1B crystalline borosilicate useful in this invention may be used as a pure material in a catalyst or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina and alumina, alone or in combination with zirconia, titania or magnesia; alumina sols; hydrated aluminas; alumina phosphates; clays such as bentonite or kaolin; or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt.% of the total composition. Catalytic compositions can contain about 0.1 wt.% to about 100 wt.% crystalline borosilicate material and preferably contain about 10 wt.% to about 80 wt.% of such material and most preferably contain about 20 wt.% to about 65 wt.% of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material. Catalytic compositions also can be made by mixing a nominally dry, cationically-exchanged crystalline borosilicate with a material, such as a metal-impregnated hydrated alumina, and then pelletizing or extruding, and calcining. This procedure can be beneficial if different metal concentrations are used on the crystalline borosilicate and the matrix.

Specific details of catalyst preparations are described in U.S. Pat. No. 4,269,813.

In a process using this invention, a stream containing a $C_2$–$C_3$ olefin, preferably propylene, is contacted with a catalytic material-containing AMS-1B borosilicate-based catalyst. Generally, in the preferable process of this invention olefin is contacted with the above-described AMS-1B borosilicate-based catalyst system in the liquid or vapor phase at a suitable reaction temperature, pressure and space velocity. Generally, suitable reaction conditions include a temperature of about 300° to about 600° C., a pressure of about 0.1 to about 50 atmospheres (10 to 5,000 kPa) or higher with hydrogen/olefin molar ratio of 0.1 to about 10 or higher at a weight hourly space velocity (WHSV) of about 0.1 to about 10 hr$^{-1}$. In a typical process scheme, a propylene-containing hydrocarbon stream is contacted with such catalyst in a reactor at about 300° to about 500° C.

at a pressure of about 2 to about 40 atmospheres (200 to 4000 kPa) with a hydrogen/propylene molar ratio of 0.1 to about 10 at a WHSV of about 0.3 to about 5 hr$^{-1}$. Preferably the propylene conversion process of this invention is conducted at about 350° to about 400° C. at a pressure of about 5 to about 20 atmospheres (500 to 2000 kPa) with a hydrogen/propylene ratio of about 0.8 to about 6 at a WHSV of about 0.5 to about 3 hr$^{-1}$.

The term "$C_2$–$C_3$ olefin" means either ethylene or propylene or a mixture thereof.

The preferable $C_2$–$C_3$ olefin feed contains predominantly propylene although typically minor amounts of ethylene and other hydrocarbons such as propane may be present. The hydrocarbon feedstream may be diluted with an inert gas such as nitrogen or helium.

This invention is demonstrated but not limited by the following Examples.

EXAMPLES I–IV

A series of molecular sieve-based catalyst compositions were prepared in which various metals were incorporated. Lanthanum-exchanged product was prepared by exchanging 30 grams of powdered AMS-1B crystalline borosilicate molecular sieve in the hydrogen form (H-AMS-1B) in 1.0 liter of 0.2 molar solution of metal nitrate with stirring overnight. This procedure was repeated twice. A final exchange solution was performed in 0.4 molar nitrate at a pH of 7 adjusted by dropwise addition of 28% aqueous ammonia. After the final exchange, the sieves were water-washed three times, mixed with sufficient water to form a slurry and added to 1200 grams of PHF alumina sol (10.3 wt.% solids) in a blender. After blending, aqueous ammonia was added to gel the sol.

A copper-exchanged molecular sieve was prepared similarly by exchanging 30.0 grams of H-AMS-1B once with one liter of 0.1 M aqueous cupric acetate solution and twice with one liter of 0.2 M aqueous cupric acetate. After the final exchange, the sieve was mixed with sufficient water to form a slurry and added to 1200 grams of PHF alumina sol (10.3 wt.% solids) and blended. Aqueous ammonia then was added to form a gel.

In all cases, gels were dried at 121° C., ground to 12–18 mesh and calcined at 538° C. in air for 24 hours. The resulting sieves were air-dried for one hour, dried at 121° C. and calcined at 538° C. in air for 24 hours.

Catalyst performance in Examples I–IV and Run A was evaluated in a fixed-bed, downflow, 18-inch by one-half inch inside diameter, Vycor reactor in which 10.0 grams of catalyst were held in place by a glass wool plug set on three dimples located twelve inches from the top of the tube. Hydrogen and hydrocarbon feed were metered individually to the reactor. Reactor effluent was analyzed through an on-line sample loop by gas chromatography. In a typical run, hydrogen flow was started and heat turned on. Twenty minutes after reaction temperature was reached, hydrocarbon was introduced and twelve minutes later the gas chromatograph sample loop was charged and injected.

Example I was run using 20 wt.% hydrogen-form AMS-1B crystalline borosilicate in a gamma alumina matrix. Examples II and III were run using a copper-exchanged and lanthanum-exchanged AMS-1B crystalline borosilicate catalyst respectively. Example IV was run with an ethylene feed using a 40 wt.% H-AMS-1B in gamma alumina catalyst composition.

Comparative Run A was performed using a 20 wt.% hydrogen-form ZSM-5 crystalline aluminosilicate in a gamma alumina matrix.

Results are shown in Table II. The data show that AMS-1B crystalline borosilicate-based molecular sieve catalysts convert propylene to other hydrocarbon products including $C_4$–$C_8$ aliphatics and $C_6$–$C_9$ aromatics with relatively low $C_1$–$C_2$ and coke production.

Table III shows analysis of product obtained by passing ethylene over a 40 wt.% H-AMS-1B crystalline borosilicate in a gamma alumina matrix at 426° C. with hydrogen. Ethylene also produces gasoline-range hydrocarbons at these conditions, but is not as reactive as propylene.

TABLE II

| Catalyst Composition | Example I H—AMS-1B | | | Ex. II Cu—AMS-1B | Ex. III LA—AMS-1B | Run A ZSM-5 |
|---|---|---|---|---|---|---|
| Conditions | | | | | | |
| Temperature (°C.) | 371 | 399 | 454 | 454 | 454 | 399 |
| WHSV (hr$^{-1}$) | 1.9 | 1.9 | 1.9 | 1.9 | 1.9 | 1.9 |
| Hydrogen/propylene (mole ratio) | 1.0 | 1.0 | 1.0 | 1.0 | 1.0 | 1.0 |
| Product Composition (wt. %) | | | | | | |
| Nonaromatic | | | | | | |
| $C_1$–$C_2$ | 1.3 | 3.3 | 5.7 | 4.8 | 5.6 | 5.2 |
| $C_3$ | 5.4 | 9.0 | 10.1 | 13.9 | 9.8 | 4.8 |
| Isobutane | 4.0 | 5.8 | 4.7 | 1.7 | 5.0 | 7.1 |
| Isobutylene, 1-butene | 5.2 | 6.8 | 7.8 | 11.0 | 7.4 | 2.7 |
| n-Butane | 1.6 | 2.8 | 2.6 | 1.7 | 2.8 | 4.5 |
| trans-2-Butene | 3.2 | 4.2 | 4.9 | 7.1 | 4.6 | 1.4 |
| cis-2-Butene | 2.6 | 3.5 | 4.3 | 6.4 | 4.1 | 1.0 |
| $C_5$ | 17.0 | 18.2 | 17.4 | 18.0 | 16.3 | 12.5 |
| $C_6$ | 15.6 | 13.6 | 11.8 | 14.9 | 8.6 | 9.4 |
| $C_7$ | 15.9 | 12.8 | 8.9 | 8.1 | 9.9 | 7.4 |
| $C_8$ | 22.2 | 11.9 | 7.5 | 3.6 | 7.1 | 9.9 |
| Aromatics | | | | | | |
| $C_6$ | 1.0 | 1.4 | 1.9 | 1.6 | 2.6 | 1.5 |
| $C_7$ | 0.9 | 1.7 | 2.7 | 2.1 | 3.1 | 5.1 |
| $C_8$ | 2.9 | 3.1 | 5.1 | 2.9 | 8.0 | 14.0 |
| $C_9$ | 1.2 | 1.9 | 4.6 | 2.2 | 5.1 | 13.5 |
| Feed Lost as Coke (mole%) | | 0.3 | 1.0 | | | |

TABLE III

| Catalyst Composition | Example IV H—AMS-1B | |
|---|---|---|
| Conditions | | |
| Temperature (°C.) | 371 | 426 |
| WHSV (hr$^{-1}$) | 2.0 | 2.0 |
| Hydrogen/ethylene (molar ratio) | 2.5 | 2.5 |
| Product Composition (wt. %) | | |
| Nonaromatic | | |
| $C_1$-$C_2$ | 39.7 | 33.8 |
| $C_3$ | 8.7 | 11.1 |
| Isobutane | 1.9 | 1.9 |
| Isobutylene, 1-butene | 10.2 | 11.1 |
| n-Butane | 0.3 | 0.4 |
| trans-2-Butene | 4.1 | 4.7 |
| cis-2-Butene | 3.0 | 3.7 |
| $C_5$ | 15.5 | 17.0 |
| $C_6$ | 7.8 | 7.7 |
| $C_7$ | 5.6 | 4.4 |
| $C_8$ | 2.1 | 3.0 |
| Aromatics | | |
| $C_6$ | 0.4 | 0.4 |
| $C_7$ | 0.4 | 0.5 |
| $C_8$ | 0.3 | 0.3 |
| $C_9$ | 0.0 | 0.0 |

EXAMPLES V AND VI

Propylene was converted according to this invention at superatmospheric pressure in a stainless steel pipe reactor approximately 30 inches in length and a one-half inch inside diameter in which hydrogen flow was controlled at 0.1 cubic foot/hour and total pressure was maintained at 14.6 atmospheres. Ten grams of catalyst were ground to 14-20 mesh (Tyler Screen) and mixed with an equal volume of finely ground Vycor before being placed in the reactor. Propylene was added to the top of the reactor as a liquid and the top portion of the reactor acted as a preheat section in which propylene was flashed to a vapor and combined with a hydrogen stream. Liquid and gaseous product were separated at high pressure and a portion of the gas recycled to the reactor. The recycle ratio was 3:1. Total liquid product was measured as weight percent of feed as shown in Table IV. The catalyst used in Example V was a copper exchanged H-AMS-1B crystalline borosilicate as described in Example II.

Zinc-exchanged catalyst used in Example VI was prepared by exchanging 100 grams of H-AMS-1B crystalline borosilicate with three liters of 0.2 M zinc acetate solution for one hour with stirring. The resulting product was filtered and similarly exchanged two more times. The product was washed four times with three liters of distilled water and dried at 121° C. Ninety grams of the resulting material was mixed with sufficient water to form a slurry and added to 3600 grams of PHF alumina sol (10 wt.% solids). After mixing, aqueous ammonia was added to gel the sol and the resulting product dried at 121° C.

TABLE IV

| | Percent Conversion to Liquid Product | |
|---|---|---|
| Catalyst Composition | Example V Cu—AMS-1B | Example VI Zn—AMS-1B |
| Time elasped (days) | | |
| 2 | | 45.0 |
| 3 | 45.5 | 50.0 |
| 4 | | 47.6 |
| 5 | 44.8 | 56.5 |
| 6 | | 42.3 |
| 7 | | 43.6 |
| 8 | 43.9 | 56.0 |
| 9 | 34.6 | |
| 10 | 45.2 | 34.6 |
| 11 | | 20.5 |
| 12 | 43.7 | 11.4 |
| 13 | 42.7 | |
| 14 | 46.1 | |
| 15 | 42.4 | |
| 16 | 41.5 | |
| 17 | — | |
| 18 | 34.8 | |
| 19 | 41.1 | |
| 20 | 30.9 | |
| Research Octane No. | 89.9 | |
| Motor Octane No. | 76.0 | |

The $C_5$ and $C_6$ fractions of the 399° C. run of Example I, the 371° C. run of Example IV, and Run A were analyzed further for specific components. The results are shown in Tables V and VI respectively and show a pronounced difference in product distributions between runs using AMS-1B and ZSM-5.

TABLE V

| | Ex. I | Ex. IV | Run A |
|---|---|---|---|
| Catalyst | | | |
| Feed | Propylene | Ethylene | Propylene |
| Temperature (°C.) | 399 | 371 | 399 |
| Product Distribution (wt. %) | | | |
| 3-methyl-1-butene | 1.4 | 1.2 | 0.4 |
| 2-methyl-1-butene | 13.2 | 0.6 | 59.9 |
| 1-pentene | 2.3 | 2.7 | 0.7 |
| 2-methyl-1-butane | 14.4 | 16.6 | 3.6 |
| n-pentane | 4.2 | 0.4 | 18.5 |
| trans-2-pentene | 10.6 | 13.7 | 2.9 |
| cis-2-pentene | 5.6 | 7.6 | 1.4 |
| 2-methyl-2-butene | 46.1 | 55.3 | 9.7 |
| Cyclopentene | 0.8 | 0.3 | 0.3 |
| Cyclopentane | 1.5 | 1.6 | 2.5 |

TABLE VI

| | Ex. I | Ex. IV | Run A |
|---|---|---|---|
| Catalyst | | | |
| Feed | Propylene | Ethylene | Propylene |
| Temperature (°C.) | 399 | 371 | 399 |
| Product Distribution (wt. %) | | | |
| 3,3-dimethyl-1-butene | 0.2 | 0.1 | 0.0 |
| 2,2-dimethylbutane | 0.1 | 0.0 | 0.3 |
| Methyl-1-pentenes | 2.0 | 9.8 | 0.4 |
| Methyl-2-pentenes | 1.9 | 5.5 | 0.9 |
| 2,3-dimethyl-1-butene | 3.2 | 3.3 | 0.6 |
| 2,3-dimethyl butane | 3.9 | 0.3 | 2.0 |
| 2-methyl pentane | 10.8 | 2.0 | 37.9 |
| 2-methyl-1-pentene | 6.4 | 7.3 | 1.1 |
| Hexene-1 | 0.6 | 0.6 | 0.0 |
| 3-methyl pentane | 4.8 | 1.9 | 15.2 |
| Hexene-3 | 5.2 | 6.7 | 0.9 |
| 3-methylcyclopentene | 5.1 | 6.7 | 0.9 |
| 2-methyl-2-pentene -methyl-2-pentene | 29.0 | 32.2 | 5.3 |
| n-hexane | 4.1 | 0.4 | 10.6 |
| 2-hexenes | 12.0 | 13.6 | 2.4 |
| Methylcyclopentane | 10.1 | 9.0 | 21.5 |

TABLE VI-continued

| | Ex. I | Ex. IV | Run A |
|---|---|---|---|
| 3,3-dimethyl-1-pentene cyclohexane | 0.0 | 0.6 | 0.0 |

What is claimed is:

1. A process to convert $C_2$–$C_3$ olefin to gasoline blending stock products comprising contacting $C_2$–$C_3$ olefin with an AMS-1B crystalline borosilicate catalyst composition which is in the hydrogen form or onto which has been placed one or more catalytically active materials selected from the group consisting of copper, lanthanum and zinc at a temperature of about 300° to about 500° C., a pressure of about 2 to about 40 atomospheres, a hydrogen to hydrocarbon molar ratio of 0.1 to about 10 and a weight hourly space velocity of about 0.3 to about 5 $hr^{-1}$.

2. The process of claim 1 wherein $C_2$–$C_3$ olefin comprises from about 1 to 100 wt.% of a feedstream contacting the catalyst.

3. The process of claim 1 wherein the AMS-1B crystalline borosilicate composition is incorporated within an alumina, silica or silica-alumina matrix.

4. The process of claim 3 wherein the AMS-1B crystalline borosilicate content in the matrix ranges from about 10 to about 80 wt.%.

5. The process of claim 6 wherein the AMS-1B crystalline borosilicate content in the matrix ranges from about 20 to about 65 wt.%.

6. The process of claim 1 wherein propylene is converted at about 350° to about 400° C. at a pressure of about 5 to about 20 atmospheres with a hydrogen/propylene ratio of about 0.8 to about 6 and a weight hourly space velocity of about 0.5 to about 3 $hr^{-1}$.

7. The process of claim 1 wherein the additional catalytically active material is copper.

8. The process of claim 1 wherein the additional catalytically active material is lanthanum.

9. The process of claim 1 wherein the additional catalytically active material is zinc.

10. The process of claim 1 wherein the AMS-1B crystalline borosilicate is in the hydrogen form.

11. The process of claim 1 wherein the $C_2$–$C_3$ olefin is ethylene.

12. The process of claim 1 wherein the $C_2$–$C_3$ olefin is propylene.

13. The process of claim 1 wherein AMS-1B crystalline borosilicate containing a catalytically active material is mixed with a matrix material.

14. The process of claim 13 wherein an additional catalytically active material is added to the AMS-1B crystalline borosilicate containing a catalytically active material mixed with the matrix.

15. The process of claim 1 wherein the AMS-1B crystalline borosilicate catalyst composition is substantially free of additional catalytically active materials.

* * * * *

UNITED STATES PATENT OFFICE
CERTIFICATE OF CORRECTION

Patent No. 4,451,685           Dated   May 29, 1984

Inventor(s)   THOMAS D. NEVITT - NORMAN F. JEROME

It is certified that error appears in the above-identified patent and that said Letters Patent are hereby corrected as shown below:

| Patent Column | Line | |
|---|---|---|
| 2 | 7 | After "and" Add -- Reissue -- |
| 7 | 8 | In Column 8, Table II, last line, "0.3" should be in Column labeled "Ex. II" and "1.0" should be in Column labeled "Ex. III." |
| 10 | 9 | In Column 10, Table IV, in entry labeled "9" "34.6" should be in Column labeled "Example VI." |
| 10 | 66 | Before "-methyl-2-pentene", Add -- 3 -- |

Signed and Sealed this

Tenth Day of December 1985

[SEAL]

Attest:

DONALD J. QUIGG

Attesting Officer        Commissioner of Patents and Trademarks